United States Patent [19]

Schütte et al.

[11] Patent Number: 5,783,203

[45] Date of Patent: Jul. 21, 1998

[54] INSECTICIDAL FERTILIZER MIXTURES

[75] Inventors: Manfred-Heinrich Schütte, Pulheim; Gerhard Baron, Leverkusen, both of Germany

[73] Assignee: Bayer Aktiengesellschaft, Leverkusen, Germany

[21] Appl. No.: 722,128

[22] PCT Filed: Apr. 3, 1995

[86] PCT No.: PCT/EP95/01222

§ 371 Date: Oct. 7, 1996

§ 102(e) Date: Oct. 7, 1996

[87] PCT Pub. No.: WO95/28370

PCT Pub. Date: Oct. 26, 1995

[30] Foreign Application Priority Data

Apr. 14, 1994 [DE] Germany ............ 44 12 833.9

[51] Int. Cl.$^6$ ............ A01N 25/00; A01N 25/34; A01N 25/08; A61K 31/54
[52] U.S. Cl. ............ 424/405; 424/408; 424/409; 514/225; 514/258; 514/341; 514/352; 514/351; 514/355; 514/356; 514/344

[58] Field of Search ............ 424/405, 408, 424/409; 514/225, 258, 341, 352, 351, 355, 356, 344

[56] References Cited

FOREIGN PATENT DOCUMENTS 0555931  2/1993  European Pat. Off. .

OTHER PUBLICATIONS

Onishi et al, 1990, Chemical Abstract, vol. 113, No. 58019f.
Ohayashi et al, 1990, Chemical Abstracts, vol. 112, No. 9757g.

*Primary Examiner*—Marian C. Knode
*Assistant Examiner*—Ali R. Salimi
*Attorney, Agent, or Firm*—Sprung Kramer Schaefer & Briscoe

[57] ABSTRACT

The present invention relates to insecticidal fertilizer mixtures comprising a fertilizer component and an agonist or antagonist of the nicotinergic acetylcholine receptors of insects.

10 Claims, No Drawings

INSECTICIDAL FERTILIZER MIXTURES

The present invention relates to insecticidal fertilizer mixtures comprising a fertilizing component and an agonist or antagonist of nicotinergic acetylcholine receptors of insects, and to their use.

Agonists or antagonists of the nicotinergic acetylcholine receptors of insects are known, for example, from the following publications:

European offenlegungsschriften Nos. 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; German Offenlegungsschriften Nos. 3 639 877, 3 712 307; Japanese Offenlegungsschriften Nos. 03 220 176, 02 207 083, 63 307 857, 63 287 764, 03 246 283, 04 9371, 03 279 359, 03 255 072; U.S. Pat. Nos. 5,034,524, 4,948,798, 4,918,086, 5,039,686, 5,034,404; PCT Applications Nos. WO 91/17,659, 91/4965; French Application No. 2 611 114; Brazilian Application No. 88 03 621.

Reference is hereby made expressly to the methods, processes, formulae and definitions described in these publications and to the individual preparations and compounds described therein.

It is known to employ fertilizers for ornamental houseplants in the form of small fertilizer sticks.

It is also known to employ insecticides for ornamental houseplants in the form of impregnated cardboard strips which are pressed into the nutrient substrate of the plant.

Also known for keeping ornamental houseplants is a tablet which contains dimethoate as insecticidal active substance and fertilizer as carrier material. The action of this mixture, however, is not completely satisfactory.

The present invention relates to:
1. Dimensionally stable mixtures of agonists or antagonists of the nicotinergic acetylcholine receptors of insects with fertilizers, adhesives and optionally auxiliaries and carrier materials in the form of small sticks, plates, tablets or granules.
2. Processes for increasing the action of agonists or antagonists of the nicotinergic acetylcholine receptors of insects, characterized in that they are employed in the form of dimensionally stable mixtures with fertilizers, adhesives and optionally auxiliaries and carrier materials.
3. Processes for the preparation of dimensionally stable mixtures of agonists or antagonists of the nicotinergic acetylcholine receptors of insects with fertilizers, characterized in that they are mixed with adhesives and optionally with auxiliaries and carrier materials and are compressed or extruded to the desired form.
4. Use of dimensionally stable mixtures of agonists or antagonists, fertilizers, adhesives and optionally auxiliaries and carrier materials for the long-term protection of plants against insect damage, by incorporating these mixtures into the nutrient medium of the plants.

The action of the agonists or antagonists of the nicotinergic acetylcholine receptors of insects in the mixtures according to the invention begins more rapidly and persists for longer than that of the customary fertilizer-free granules. The mixtures according to the invention can be employed simply and without problems, specifically in non-commercial horticulture.

Some agonists or antagonists of the nicotinergic acetylcholine receptors of insects are covered by the class of nitromethylenes and related compounds.

These compounds can be represented preferably by the general formula (I)

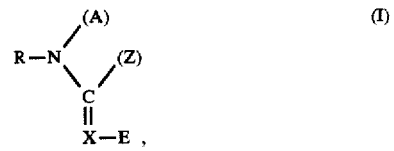

in which
R represents hydrogen or optionally substituted radicals from the group acyl, alkyl, aryl, aralkyl, heteroaryl or heteroarylalkyl;

A represents a monofunctional group from the series consisting of hydrogen, acyl, alkyl, aryl or represents a bifunctional group which is linked to the radical Z;

E represents an electron-withdrawing radical;

X represents the radicals —CH= or =N—, it being possible for the radical —CH= to be linked to the radical Z instead of one H atom;

Z represents a monofunctional group from the series consisting of alkyl, —O—R, —S—R,

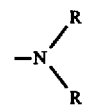

or represents a bifunctional group which is linked to the radical A or to the radical X.

Particularly preferred compounds of the formula (I) are those in which the radicals have the following meaning:

R represents hydrogen and represents optionally substituted radicals from the series consisting of acyl, alkyl, aryl, aralkyl, heteroaryl, heteroarylalkyl.

Acyl radicals which may be mentioned are formyl, alkylcarbonyl, arylcarbonyl, alkylsulphonyl, arylsulphonyl, (alkyl-)-(aryl-)-phosphoryl, which may in turn be substituted.

Alkyl which may be mentioned is $C_{1-10}$-alkyl, in particular $C_{1-4}$-alkyl, specifically methyl, ethyl, i-propyl, sec.- or t.-butyl, which may in turn be substituted.

Aryl which may be mentioned is phenyl, naphthyl, especially phenyl.

Aralkyl which may be mentioned is phenylmethyl, phenethyl.

Heteroaryl which may be mentioned is heteroaryl having up to 10 ring atoms and N, O, S, in particular N as heteroatoms. Thiophenyl, furyl, thiazolyl, imidazolyl, pyridyl, benzothiazolyl may be mentioned specifically.

Heteroarylalkyl which may be mentioned is heteroarylmethyl, heteroarylethyl having up to 6 ring atoms and N, O, S, in particular N, as heteroatoms.

Substituents which may be listed by way of example and preference are: alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms, and preferably 1 to 5, in particular 1 to 3, halogen atoms, the halogen atoms being identical or different and the halogen atoms preferably being fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2 carbon atoms per alkyl group, such as methylamino, methyl-ethylamino, n- and i-propylamino and methyl-n-butylamino; carboxyl; carboalkoxy having preferably 2 to 4, in particular 2 or 3 carbon atoms, such as carbomethoxy and carboethoxy; sulpho (—SO$_3$H); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl, and heteroarylamino and heteroarylalkylamino, such as chloropyridylamino and chloropyridylmethylamino.

A particularly preferably represents hydrogen and represents optionally substituted radicals from the series consisting of acyl, alkyl, aryl, which preferably have the meanings given for R. A additionally represents a bifunctional group. Optionally substituted alkylene having 1–4, in particular 1–2, C atoms may be mentioned, substituents which may be mentioned being the substituents listed further above, and it being possible for the alkylene groups to be interrupted by heteroatoms from the series consisting of N, O, S.

A and Z may form, together with the atoms to which they are attached, a saturated or unsaturated heterocyclic ring. The heterocyclic ring may contain a further 1 or 2 identical or different heteroatoms and/or hetero groups. The heteroatoms are preferably oxygen, sulphur or nitrogen and the hetero groups are preferably N-alkyl, the alkyl of the N-alkyl group preferably containing 1 to 4, in particular 1 or 2, carbon atoms. Alkyl which may be mentioned is methyl, ethyl, n- and i-propyl and n-, i- and t-butyl. The heterocyclic ring contains 5 to 7, preferably 5 or 6, ring members.

Examples which may be mentioned of the heterocyclic ring are pyrrolidine, piperidine, piperazine, hexamethyleneimine, hexahydro-1,3,5-triazine, morpholine, which may optionally be substituted preferably by methyl.

E represents an electron-withdrawing radical, particular mention being made of NO$_2$, CN, halogenoalkylcarbonyl such as 1,5-halogeno-C$_{1-6}$-carbonyl, in particular COCF$_3$.

X represents —CH= or —N=

Z represents optionally substituted radicals alkyl, —OR, —SR, —NRR, where R and the substituents preferably have the meaning given above.

Z is able to form, apart from the abovementioned ring, together with the atom to which it is attached and the radical $$=\overset{|}{C}-$$

in the place of X, a saturated or unsaturated heterocyclic ring. The heterocyclic ring may contain a further 1 or 2 identical or different heteroatoms and/or hetero groups. Heteroatoms are preferably oxygen, sulphur or nitrogen and hetero groups are preferably N-alkyl, the alkyl or N-alkyl group preferably containing 1 to 4, in particular 1 or 2, carbon atoms. Alkyl which may be mentioned is methyl, ethyl, n- and i-propyl and n-, i-, and t-butyl. The heterocyclic ring contains 5 to 7, preferably 5 or 6, ring members.

Examples which may be mentioned of the heterocyclic ring are pyrrolidine, piperidine, piperazine, hexamethyleneimine, morpholine and N-methylpiperazine.

Compounds which may be mentioned and which it is possible to use with very particular preference in accordance with the invention are compounds of the general formulae (II) and (III):

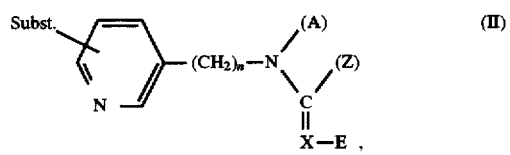

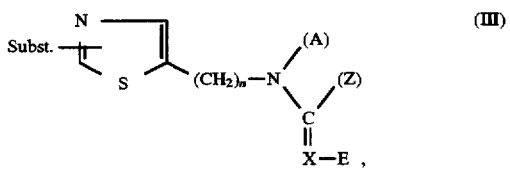

in which n represents 1 or 2,

Subst. represents one of the substituents listed above, in particular halogen and very particularly chlorine, A, Z, X and E have the meanings given above, The following compounds may be mentioned specifically:

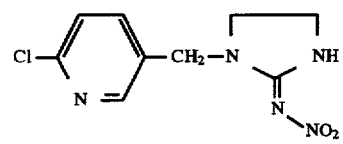

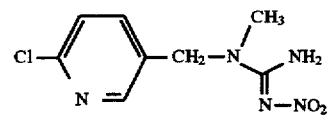

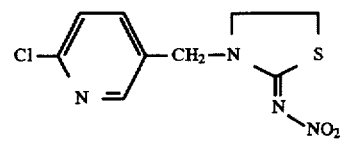

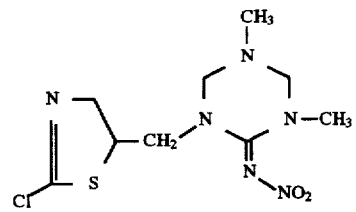

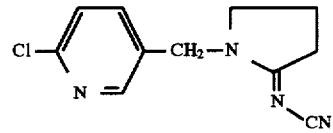

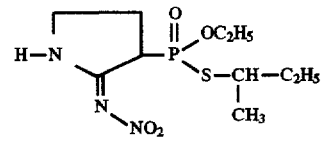

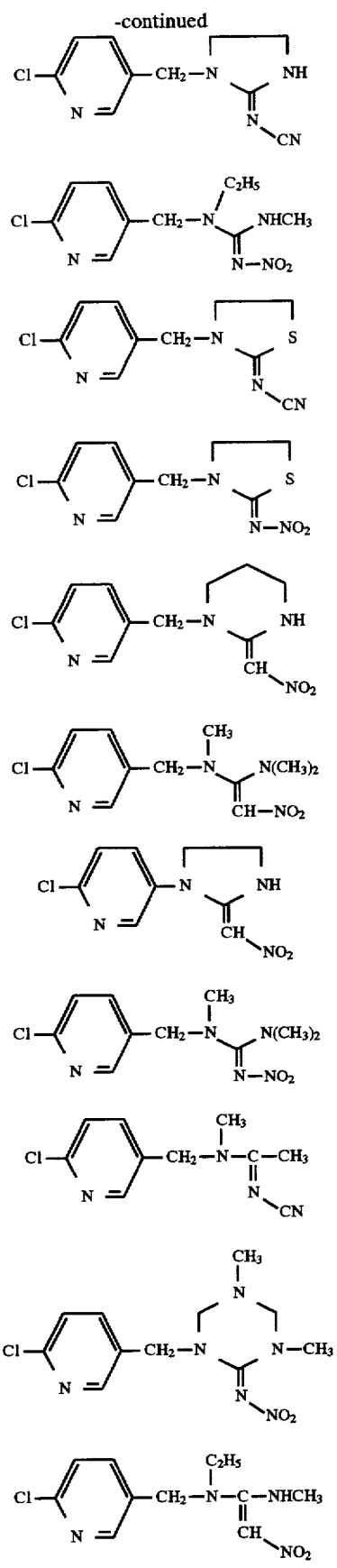

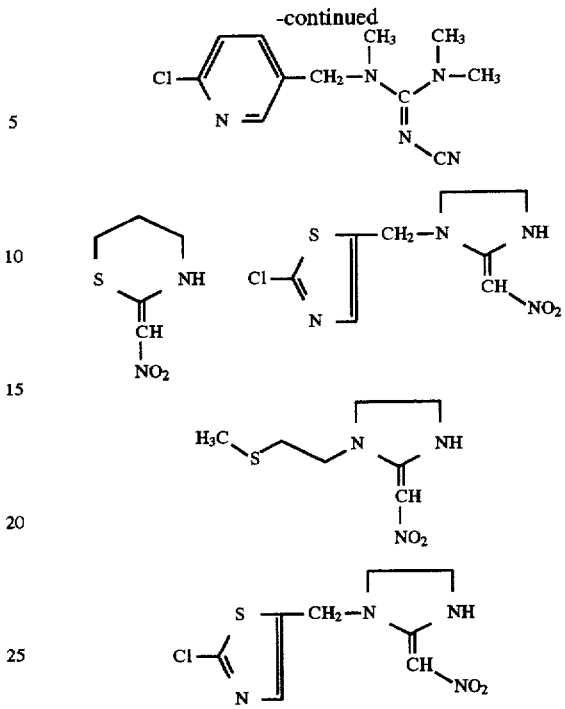

The contents of active substance are between 0.01 to 10%, in particular between 0.1 to 2.5%.

Fertilizer components which may be used are organic and inorganic nitrogen-containing compounds such as urea, urea-formaldehyde condensation products, amino acids, ammonium salts and nitrates, and also potassium salts (preferably chlorides, sulphates, nitrates) and phosphoric acid and/or salts of phosphoric acids (preferably potassium salts and ammonium salts). The fertilizers may also contain salts of micronutrients (preferably manganese, magnesium, iron, boron, copper, zinc, molybdenum and cobalt) and phytohormones (e.g. vitamin B1 and indole-III-acetic acid). The commercially available complete fertilizers are preferably employed.

The principal fertilizer constituents, nitrogen, potassium and phosphorus, can be varied within wide limits. It is conventional to use contents of from 1 to 30% of nitrogen (preferably from 5 to 20%), from 1 to 20% of potassium (preferably from 3 to 15%) and from 1 to 20% of phosphorus (preferably from 3 to 10%). The contents of microelements are usually in the ppm range, preferably from 1 to 1000 ppm.

Adhesives which may be mentioned are tackifiers such as carboxymethylcellulose, natural and synthetic polymers in the form of powders, granules or latices, polyvinylpyrrolidone, vinylpyrrolidone-styrene copolymers, vinylpyrrolidon-vinylacetat copolymers, polyethyleneglycols or inorganic adhesives such as gypsum or cement. They are present in the mixture in concentrations of from 1 to 30% by weight, preferably from 2 to 20% by weight.

Suitable solid carrier materials are, for example, natural ground minerals such as kaolins, aluminas, talc, chalk, quartz, attapulgite, montmorillonite or diatomaceous earth and synthetic ground minerals such as highly dispersed silicic acid, aluminium oxide and silicates, in addition calcium-phosphates and calcium-hydrogen-phosphates. Suitable solid carrier materials for granules are, for example, crushed and fractionated natural minerals such as calcite, marble, pumice, sepiolite, dolomite and synthetic granules of inorganic and organic ground materials, and also granules of organic material such as sawdust, coconut husks, corn cobs and tobacco stalks.

Further auxiliaries for the preparation of the mixtures according to the invention are disintegrants and surfactants.

Disintegrants are employed in order to promote the release of the active substance in the soil. Corn starch, crosslinked polyvinylpyrrolidone and specific celluloses are used individually or in combination. The disintegrants are present in concentrations of from 1 to 20% by weight, preferably from 3 to 10% by weight.

Surfactants are employed in order to improve the biological activity of the active substance by solubilization; their content is between 1 to 10% by weight, preferably from 2 to 5% by weight. Nonionic surfactants of the alkyl-aryl-ethoxylate type are appropriate.

The mixtures of active substance, fertilizers, adhesive, auxiliary and inert substances are mixed intensively and compressed by an extruder into small sticks with a diameter of from 3 to 10 mm, preferably from 6 to 8 mm, and a length of from 1 to 10 cm, preferably from 3 to 6 cm. Alternatively, the mixture can be brought into the desired form of small sticks using a tableting press. It is also possible first of all to produce small sticks or tablets which are free from active substance and to coat these sticks or tablets, in a second step, with a solution of the active substance. This subsequent coating operation can also be used with advantage to apply active substance to fertilizer granules.

EXAMPLES

A mixture of 1.
    0.25% imidacloprid
    2.40% pyrrolidone-styrene copolymer
    2.30% tristyrylphenyl 16-ethoxylate
    0.80% talc A
    5.00% corn starch
    38.00% Triabon complete fertilizer (BASF)
    40.00% kaolin
    about 11.00% water is thoroughly mixed in a kneading apparatus and then compressed in an extruder to give small sticks with a diameter of about 6 mm which are cut to a length of about 4 cm. After drying (40° C., 6 hours) the small sticks have the desired strength.

2.
    2.5% imidacloprid
    4.8% pyrrolidone-styrene copolymer
    2.3% tristyrylphenyl 16-ethoxylate
    0.8% talc
    5.0% corn starch
    36.0% Nitrophoska-permanent complete fertilizer
    38.0% kaolin
    about 11.0% water Preparation as for Example 1.

3. A mixture like Example 1 or 2 is brought without water into the desired form, in a tableting press.

4. The complete fertilizers Triabon and Nitrophoska-permanent, respectively, in commercially available granulated form, are sprayed in a gravity mixer with a solution of imidocloprid in acetone, and dried. The active substance is located on the granule surface.

The fertilizer mixtures according to the invention are suitable for the control of insects which are encountered in horticulture, in agriculture and in forests. They are active against normally sensitive and resistant species and against all or individual stages of development. The abovementioned pests include:

From the order of the Isopoda, for example *Oniscus asellus, Armadillidium vulgare* and *Porecellio scaber.*

From the order of the Diplopoda, for example, *Blaniulus guttulatus.*

From the order of the Chilopoda, for example, *Geophilus carpophagus* and *Scutigera spec.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria.*

From the order of the Dermaptera, for example, *Forficula auricularia.*

From the order of the Isoptera, for example *Reticulitermes spp.*

From the order of the Mallophaga, for example, *Trichodectes spp.* and *Damalinea spp.*

From the order of the Thysanoptera, for example, *Hercinothrips femoralis* and *Thrips tabaci.*

From the order of the Heteroptera, for example, *Eurygaster spp., Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, malacosoma neustria, Euproctis chrysorrhoea, Lymantria spp., Bucculatrix thurberiella, Phyllocnistis citrella, Agrotis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus pp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica.*

From the order of the Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster,*

*Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tanaus* spp., *Tannia* spp., *Bibio hortulanus*, *Oscinella frit*, *Phorbia* spp., *Pegomyia hyoscyami*, *Ceratitis capitata*, *Dacus oleae* and *Tipula paludosa*.

Particularly worthy of mention is the action against aphids and whitefly in market gardening and non-commercial horticulture.

The shaped articles according to the invention are employed in a dose such that, per liter of treated earth or nutrient medium, from about 1 to 2000 mg of active substance, preferably from 1 to 100 mg of active substance and particularly preferably from 1 to 50 mg of active substance are employed.

EXAMPLE 10 poinsettia plants which were heavily infested with whitefly were treated with different formulations of the active substance imidacloprid. The action was observed 18 to 70 days after the treatment. The following treatments are carried out:

A: Imidacloprid granules, 5%, in a dose of 50 mg/l of earth, were incorporated into the surface of the planted earth.

B: Imidacloprid granules, 5%, in a dose of 25 mg/l of earth, were incorporated into the surface of the planted earth.

C: Imidacloprid granules, 5%, in a dose of 5 mg/l of earth, were incorporated into the surface of the planted earth.

D: Small Triabon sticks with 2.5% of imidacloprid of composition 1 (above) were stuck into the planted earth in a dose of 50 mg/l of earth.

E: Small Triabon sticks with 2.5% of imidacloprid of composition 1 (above) were stuck into the planted earth in a dose of 25 mg/l of earth.

F: Small Triabon sticks with 2.5% of imidacloprid of composition 1 (above) were stuck into the planted earth in a dose of 5 mg/l of earth.

The following results were obtained:

| Treatment | Result after days in % action compared with the untreated control | | | | | |
|---|---|---|---|---|---|---|
| | 18 | 22 | 28 | 42 | 49 | 70 |
| A | 22 | 85 | 100 | 100 | 100 | 100 |
| B | 14 | 76 | 100 | 100 | 100 | 100 |
| C | 13 | 56 | 60 | 75 | 79 | 95 |
| D | 9 | 78 | 100 | 100 | 100 | 100 |
| E | 4 | 64 | 100 | 100 | 100 | 100 |
| F | 0 | 52 | 98 | 100 | 100 | 100 |

100% denotes complete action, 0% denotes no action.

We claim:

1. An insecticidal fertilizer mixture comprising:

(a) an agonist or antagonist of the nicotinergic acetylcholine receptor of an insect;

(b) a fertilizer; and (c) an adhesive;

said mixture being in the form of a stick, plate, tablet or granule.

2. The mixture according to claim 1 wherein said agonist or antagonist is a compound of formula (I)

$$R-N\begin{matrix}(A)\\ \\(Z)\end{matrix}\phantom{X}\text{(I)}$$
$$\phantom{R-N}\underset{\|}{C}$$
$$\phantom{R-N}X-E,$$

in which

R represents hydrogen or optionally substituted radicals from the group acyl, alkyl, aryl, aralkyl, heteroaryl or heteroarylalkyl;

A represents a monofunctional group selected from the group consisting of hydrogen, acyl, alky, and aryl or represents a bifunctional group which is linked to the radical Z;

E represents an electron-withdrawing radical;

X represents the radicals —CH= or =N—, wherein the radical —CH= may be linked to the radical Z instead of one H atom;

Z represents a monofunctional group selected from the group consisting of alkyl, —O—R, —S—R, and $$-N\begin{matrix}R\\ \\R\end{matrix}$$

or represents a bifunctional group which is linked to the radical A or to the radical X.

3. The mixture according to claim 2 wherein said agonist or antagonist is a compound of formula (I) wherein R represents hydrogen and represents optionally substituted radicals selected from the group consisting of acyl, alkyl, aryl, aralkyl, heteroaryl, and heteroarylalkyl wherein Acyl radicals are formyl, alkylcarbonyl, arylcarbonyl, alkylsulphonyl, arylsulphonyl, or (alkyl-)-(aryl-)-phosphoryl, which may be substituted;

Alkyl radicals are $C_{1-10}$-alkyl, which may be substituted;

Aryl is phenyl or naphthyl;

Aralkyl is phenylmethyl, or phenethyl;

Heteroaryl is heteroaryl having up to 10 ring atoms and N, O, S as heteroatoms;

Heteroarylalkyl is hetero-arylmethyl, or heteroarylethyl having up to 6 ring atoms and N, O, S as heteroatoms;

wherein the substitutions in the acyl radicals and alkyl radicals are $C_1$–$C_4$ alkyl, $C_1$–$C_4$ alkoxy, $C_1$–$C_4$ alkylthio, $C_1$–$C_4$ halogenoalkyl, the halogen atoms being identical or different and the halogen atoms being fluorine, chlorine and bromine; hydroxyl; halogen; cyano; nitro; amino; $C_1$–$C_4$ monoalkyl- and $C_1$–$C_4$ dialkylamino; carboxyl; $C_2$–$C_4$ carboalkoxy; $C_1$–$C_4$ alkylsulphonyl; $C_6$–$C_{10}$ arylsulphonyl; and heteroarylamino and heteroarylalkylamino;

A represents hydrogen and represents optionally substituted radicals from the series consisting of acyl, alkyl, and aryl;

A and Z may form, together with the atoms to which they are attached, a saturated or unsaturated heterocyclic ring comprising 1 or 2 identical or different heteroatoms or hetero groups, wherein the heteroatoms are oxygen, sulphur or nitrogen and the heterogroups are $C_2$–$C_4$ N-alkyl; wherein alkyl is methyl, ethyl, n- and i-propyl and n-, i- and t-butyl; wherein the heterocyclic ring comprises 5 to 7 ring members;

E represents an electron-withdrawing radical, selected from the group consisting of NO$_2$, CN, and alkylcarbonyl;

X represents —CH= or —N=;

Z represents optionally substituted radicals alkyl, —OR, —SR, or —NRR, wherein R and the substitutions have the meanings given above; and Z is able to form, apart from the abovementioned ring, together with the atom to which it is attached and the radical $$=\overset{|}{C}-$$

in the place of X, a saturated or unsaturated heterocyclic ring which may contain 1 or 2 identical or different heteroatoms or hetero groups, wherein the heteroatoms are oxygen, sulphur or nitrogen and hetero groups are $C_2$–$C_4$ N-alkyl and wherein the heterocyclic ring contains 5 to 7 ring members.

4. The mixture according to claim 2 wherein said agonist or antagonist is a compound of formula (II)

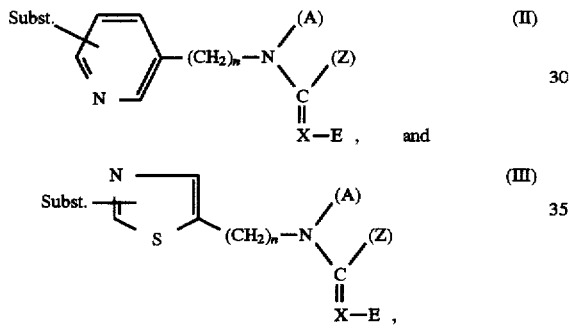

in which n represents 1 or 2,

Subst. has the meaning given above in claim 2 for subsitutions; and

A, Z, X and E have the meanings given above in claim 2.

5. The mixture according to claim 1 wherein said agonist or antagonist is a compound selected from the group consisting of

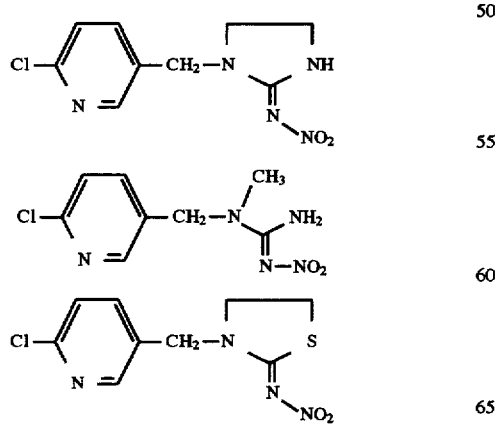

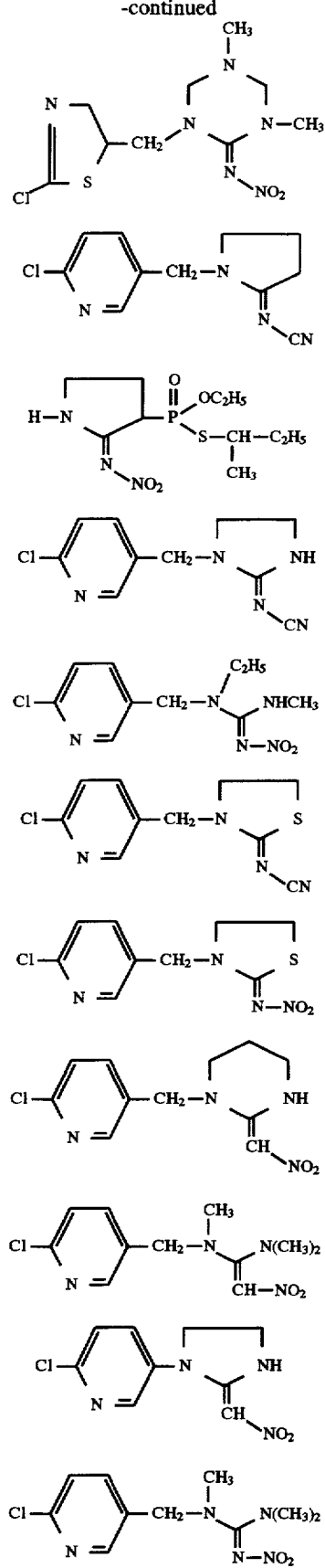

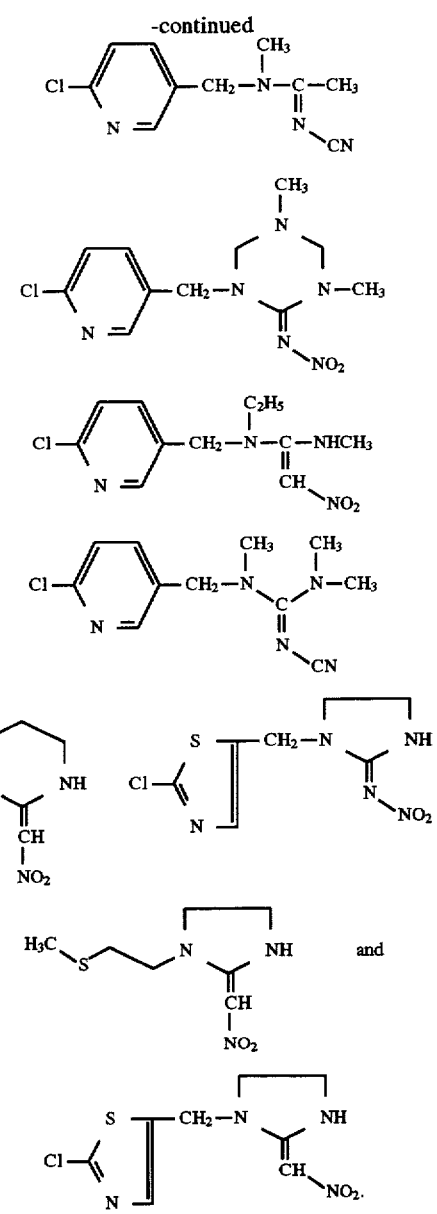

6. A process for the preparation of an insecticidal fertilizer mixture comprising (a) mixing an agonist or antagonist of the nicotinergic acetylcholine receptor of an insect with a fertilizer and an adhesive and optionally adding disintegrants and surfactants and carriers, and (b) compressing or extruding said mixture into a desired form.

7. A method for the protection of plants from unwanted insects which comprises adding an insecticidally effective amount of the mixture according to claim 1 into the nutrient medium of such plants.

8. An insecticidal fertilizer mixture comprising:

(a) a compound of the formula

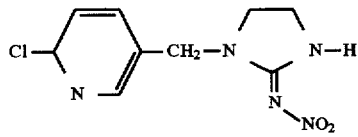

(b) a fertilizer; and (c) an adhesive;

said mixture being in the form of a stick, plate, tablet or granule.

9. A process for the preparation of an insecticidal fertilizer mixture comprising (a) mixing a compound of the formula

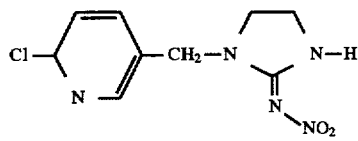

with a fertilizer and an adhesive and optionally adding disintegrants and surfactants and carriers and (b) compressing or extruding said mixture into a desired form.

10. A method for the protection of plants from unwanted insects which comprises adding an insecticidally effective amount of the mixture according to claim 8 into the nutrient medium of such plants.

* * * * *